(12) United States Patent
Chaibi

(10) Patent No.: US 8,546,084 B2
(45) Date of Patent: Oct. 1, 2013

(54) DEVICE AND METHOD FOR IDENTIFYING AND DETERMINING BLOOD GROUPS

(75) Inventor: Najim Chaibi, Bordeaux (FR)

(73) Assignee: ABO Diag, Martillac (FR)

( * ) Notice: Subject to any disclaimer, the term of this patent is extended or adjusted under 35 U.S.C. 154(b) by 453 days.

(21) Appl. No.: 12/667,321

(22) PCT Filed: Jul. 2, 2008

(86) PCT No.: PCT/FR2008/051232
§ 371 (c)(1),
(2), (4) Date: Dec. 30, 2009

(87) PCT Pub. No.: WO2009/007649
PCT Pub. Date: Jan. 15, 2009

(65) Prior Publication Data
US 2010/0184102 A1      Jul. 22, 2010

(30) Foreign Application Priority Data

Jul. 2, 2007   (FR) ..................................... 07 04741

(51) Int. Cl.
*G01N 33/53*        (2006.01)
(52) U.S. Cl.
USPC .............................. 435/7.1; 435/7.2; 436/501
(58) Field of Classification Search
None
See application file for complete search history.

(56) References Cited

U.S. PATENT DOCUMENTS

| | | | | |
|---|---|---|---|---|
| 5,028,332 A | * | 7/1991 | Ohnishi | 210/500.34 |
| 5,030,555 A | * | 7/1991 | Clemmons | 435/5 |
| 5,064,541 A | * | 11/1991 | Jeng et al. | 210/767 |
| 5,096,809 A | | 3/1992 | Chen et al. | |
| 5,126,276 A | | 6/1992 | Fish et al. | |
| 5,187,100 A | * | 2/1993 | Matzinger et al. | 436/16 |
| 5,710,049 A | | 1/1998 | Noppe et al. | |
| 7,115,421 B2 | * | 10/2006 | Grzeda et al. | 436/70 |
| 7,744,820 B2 | * | 6/2010 | Togawa et al. | 422/535 |
| 8,030,006 B2 | * | 10/2011 | Robb et al. | 435/7.1 |
| 8,053,226 B2 | * | 11/2011 | Schwind et al. | 435/287.2 |
| 2004/0096356 A1 | | 5/2004 | Degelaen | |
| 2006/0016747 A1 | * | 1/2006 | Sakaino et al. | 210/450 |
| 2006/0088941 A1 | * | 4/2006 | Law et al. | 436/63 |
| 2006/0105402 A1 | * | 5/2006 | Rott et al. | 435/7.21 |

FOREIGN PATENT DOCUMENTS

| | | | |
|---|---|---|---|
| GB | 2250342 | * | 3/1996 |
| WO | WO 2004/103939 A2 | | 12/2004 |
| WO | WO-2005005991 | * | 1/2005 |
| WO | WO 2006/098803 A1 | | 9/2006 |

OTHER PUBLICATIONS

International Search Report, dated Jan. 21, 2009, from corresponding PCT application.
R.C. Knight et al., Abstract of "Detection of red cell antibodies: current and future techniques", British Journal of Biomedical Science, 1995.

* cited by examiner

*Primary Examiner* — Jacob Cheu
(74) *Attorney, Agent, or Firm* — Young & Thompson

(57) ABSTRACT

A device for the determination and/or the detection of erythrocyte blood groups from a whole blood sample, and a process that implements this device, as well as a kit for the determination and the detection of blood groups are disclosed.

14 Claims, 1 Drawing Sheet

DEVICE AND METHOD FOR IDENTIFYING AND DETERMINING BLOOD GROUPS

FIELD OF THE INVENTION

This invention relates to a device for the identification and the determination of erythrocyte antigens of blood groups and corresponding plasmatic antibodies from a whole blood sample.

The purpose of the invention is also the use of this device, a process that implements this device, as well as a kit for determination of the blood groups.

BACKGROUND OF THE INVENTION

Blood is a connective liquid tissue that is present in man and the majority of evolved animals. Despite an identical cellular composition, there is a variability of various elements of the blood, defined by different antigenic systems called blood groups.

In practice, the focus more particularly is on erythrocyte blood groups, antigen systems that are located on the surface of red blood cells, such as, for example, the ABO, rhesus, Kell, Duffy, MNS, and Lewis systems, etc.

Conventionally, the determination of a blood group is done on antigen-antibody recognition. When a specific antibody of the antigen recognizes the latter, it is fixed. Generally, the antibodies that are used in the recognition of the blood groups are IgM immunoglobulins that clump the red blood cells. The conventionally used techniques consist in seeking and identifying the presence or absence of antigens of the blood group on the surface of the erythrocytes or in seeking and identifying the presence or the absence of anti-antigenic antibodies of the blood group in the plasma.

In particular, for the ABO system, the Beth Vincent test makes it possible to determine the antigens that are borne by the red blood cells, and the complementary Simonin-Michon test or serum-check test makes it possible to determine the antibodies that circulate in the serum.

In the Beth Vincent test, the red blood cells of the individual, obtained after phase separation of the cells and the plasma, either by centrifuging or by decanting, are brought into the presence of antibody reagents of a known specificity. Generally, this test is made visible by observation of clumping red blood cells when the antibodies recognize the corresponding erythrocyte antigens.

In the Simonin test, the plasma of the individual is brought into the presence of test red blood cells that each belong to a specific antigen group of the ABO system. It involves a test for clumping the plasma of the individual with test erythrocytes.

For the research of so-called irregular antibodies or RAI, detecting the presence or the absence of immunoglobulins directed against various erythrocyte antigens of the individual in the blood of an individual is involved. For this purpose, an attempt is made to demonstrate the attachment of these immunoglobulins to test red blood cells whose antigens are known, with the direct and indirect Coombs technique, whereby the comparison of the results makes it possible to deduce the presence or the absence of immunoglobulins.

There are a large number of processes and devices used for phenotyping in the field of immunology-hematology, whereby the techniques can be manual, on an opaline plate, in a microplate tube or cup, or else completely automated using a robot for distributing samples and reagent, stirring, incubating and automatic reading. Two reference techniques in particular are known: the microplate techniques and the test gel filtration techniques.

However, these existing techniques for phenotyping blood groups have numerous drawbacks.

The microplate techniques, for example, require a stirring phase that is critical because the simultaneously present multiple reactions on the substrate do not have the same resuspension kinetics. They should be produced under visual monitoring, and it is necessary to be particularly attentive to the adhesion phenomena of certain reagents.

Likewise, during the implementation of test gel filtration techniques, there is also a risk of not detecting certain agglutinations, in particular during the plasmatic test of the ABO group. Another drawback is the too-frequent detection of autoantibodies in relation to the test erythrocyte preparations, in particular those that are treated by proteolytic enzymes.

In addition, all of these techniques have a major drawback because they require a preliminary centrifuging of the whole blood so as to separate the constituent elements of the blood, a restrictive stage that greatly increases the time and the cost of analysis and that requires the use of centrifuges that are bulky and difficult to handle.

So as to eliminate this heavy centrifuging stage, variants have been developed, based on the use of magnetic particles.

By way of example, it is possible to cite the patent application EP-0,351,857 that describes a process for immunological metering that uses magnetized markers such as antibodies or antigens that are fixed to the magnetic latex balls. In particular, an RAI technique by immunoadhesion is described in which a magnetic field is applied to erythrocytes that are previously fixed to the bottom of a microplate cup, sensitized with the serum to be tested, washed and mixed with magnetic latex balls that are coated with an anti-immunoglobulin. The application EP 0,230,768 that describes a process for co-aggregation of magnetic particles that are able to link to a substance that is contained in a sample by means of polycationic compounds in the presence of a magnetic field is also known.

However, these different techniques also have numerous drawbacks. They are difficult and take a long time to implement, are not very economical, and require the use of devices that are complex and not very mobile.

SUMMARY OF THE INVENTION

Also, the purpose of this invention is to eliminate the drawbacks of the prior art by proposing a simple and effective means for phenotyping erythrocyte blood groups, and the identification and the determination of corresponding plasmatic antibodies, having a precision and an exactitude that are at least comparable to those obtained by the reference methods.

In particular, the objective of the invention is to propose an economical system, easy to use, automatable and mobile, able to quickly determine and detect erythrocyte blood groups by immobilization of red blood cells directly from a whole blood sample, without using centrifuging equipment and/or any measuring device.

To meet this objective, this invention proposes a device for the identification and the determination of blood groups from a whole blood sample, comprising a solid substrate that comprises at least one reactive zone, whereby said reactive zone consists of at least one porous polymer membrane, having pores with a diameter of between 1 and 20 µm, designed to be impregnated by at least one complexing reagent, and an absorbent membrane, designed to recover excess blood from the sample that is analyzed. The device makes it possible to identify and determine erythrocyte antigens of blood groups and/or corresponding plasmatic antibodies.

The purpose of the invention is also the use of this device, as well as a process for phenotyping erythrocyte blood groups by immobilization reaction of red blood cells, implementing this device.

Advantageously, this invention makes it possible to quickly detect and/or to determine an erythrocyte blood group, directly from whole blood, by a result from reading by positivity, without using a centrifuge or measuring equipment. The device makes possible simultaneous detection of the antigens of blood groups and corresponding plasmatic antibodies.

According to a final aspect, the invention also relates to a kit for the identification and the determination of erythrocyte antigens of blood groups and corresponding plasmatic antibodies.

BRIEF DESCRIPTION OF THE DRAWINGS

Other characteristics and advantages will emerge from the following description of the invention, a description that is provided by way of example only, relative to the accompanying drawings in which.

DETAILED DESCRIPTION OF THE INVENTION

The device according to the invention is designed for the determination and/or the detection of erythrocyte blood groups from a whole blood sample. As shown in the figures, it comprises a solid substrate 1 that comprises at least one reactive zone 4, whereby said reactive zone consists of at least:
- One porous polymer membrane 3 that has pores with a diameter of between 1 and 20 µm, designed to be impregnated by at least one complexing reagent, and
- One absorbent membrane 2 that is designed to recover excess blood from the analyzed sample.

The porous polymer membrane 3 has pores with a diameter of between 1 and 20 µm, preferably between 1 and 14 µm.

According to a preferred embodiment, the porous membrane 3 is transparent. It can be a high-density polyethylene membrane that has characteristics that are particularly suited to the invention, in particular for the activation and the immobilization of the antibodies. Even more preferably, the porous membrane 3 is such that it has a good resistance, a rapid migration speed that corresponds to the adsorption of a drop of whole blood in less than 10 seconds, and a mean porosity of 7 µm.

The membrane 3 is designed to be impregnated with complexing reagents. By way of example, in the case where the device is used for a Beth Vincent test, the membrane 3 is impregnated with monoclonal antibody reagents, such as the antibodies anti-A1, anti-A2, anti-B, anti-AB, or anti-D; in the case where the device is used for a Simonin test, the membrane 3 is impregnated with antiglobulin reagents or lectins. The complexing reagents are linked specifically to the activity zone.

The complexing reagents are fixed on the membrane 3 by any suitable means. In particular, they can be fixed by passive and selective adsorption. This selectivity improves the accuracy and the precision of the test.

Figure 1:
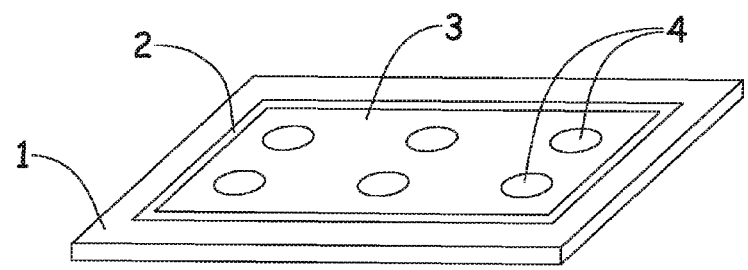
FIG. 1 shows a diagram of the device according to the invention, seen in perspective.
Figure 2A:
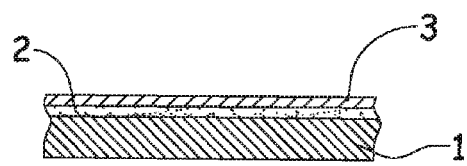
FIG. 2a shows a diagrammatic cutaway of a first embodiment of a reactive zone of a device according to the invention.
Figure 2B:
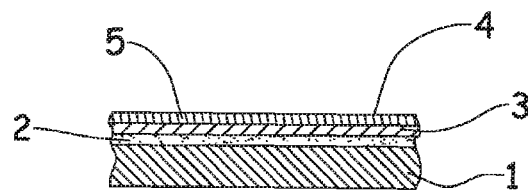
FIG. 2b shows a diagrammatic cutaway of a second embodiment of a device according to the invention.

According to a variant that is illustrated in FIG. 2b, the reactive zone(s) 4 of the device also comprise a filter 5. This filter can consist of, for example, glass fibers with a diameter of between 1 and 7 µm.

When the device is used for the identification and the determination of antibodies in the plasma of the individual, this filter 5 is preferably impregnated by reagents that can clump the erythrocytes so as to retain the red blood cells and to allow only the plasma to pass when the whole blood is deposited. By way of example, these reagents can be soybean agglutinins, lectins or any other substance that may or may not be biological and that makes it possible to clump red blood cells.

These agglutination reagents are fixed on the filter 5 by any suitable means. In particular, they can be fixed by adsorption.

Figure 3:
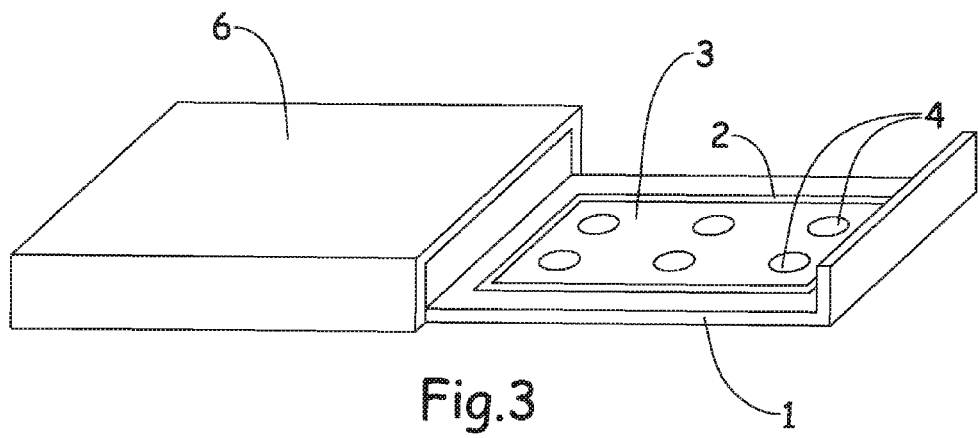
FIG. 3 shows a perspective view of an embodiment of the device according to the invention.

According to a particular embodiment of the invention shown in FIG. 3, the device also comprises a reservoir 6 that contains a washing and/or revealing solution. This reservoir can be fixed integrally to the device.

The device according to the invention can be used to determine and/or to detect blood groups, in particular ABO, rhesus and RAI blood groups, starting from a whole blood sample.

The device according to the invention can be used in particular for the implementation of a process for phenotyping erythrocyte blood groups by reaction for immobilization of erythrocytes, comprising the following stages:
 Depositing a whole blood sample on a reactive zone 4,
 Allowing the reaction to proceed for at least 30 seconds, and
 Applying a washing solution so as to elute the elements that are not linked to the porous membrane 3.

When the blood is deposited on the reactive zone 4, the blood elements that can be linked specifically to the complexing reagents of the porous membrane 3 are picked up on said membrane. When the washing solution is applied, such as a PBS-Tween washing solution, the elements of the blood that are not fixed on the membrane 3 are eliminated toward the buffer membrane 2.

Reading of the result is done by positivity in a macroscopic manner. If the erythrocytes are immobilized on the porous membrane 3, the result is reflected by a coloring of the reactive zone 4.

According to one embodiment of the invention that is particularly suited to the phenotyping of ABO, rhesus and RAI blood groups, the membrane 3 is impregnated by specific anti-antigenic antibody reagents of the erythrocytes, such as, for example, the anti-A1, anti-A2, anti-B, anti-AB or anti-D antibodies. The membrane 3 then acts as a trap for the red blood cells that makes possible their fixing on the immunoglobulins that are previously fixed on the reactive zone. The antibody reagents that are linked specifically to the reactive zone make possible a picking-up of red blood cells that involves an immobilization of the latter. In addition, this phenomenon is amplified by an actual agglutination due to several antibody residues that are not eluted by the washing solution.

When the red blood cells of the blood sample that is deposited on the reactive zone bear antigens that correspond to the antibody that is present in the reactive zone, there is a reaction of picking up and immobilizing the red blood cells that is reflected visually by a red coloring of the reactive zone.

When the red blood cells are not recognized by the corresponding antibodies, they are eluted to the buffer membrane 2, and there is an absence of coloring in the reactive zone.

Advantageously, this process does not use a coloring technique for the revealing and reading of the result, or the particular device for observing agglutination.

In addition, the process according to the invention makes it possible to avoid pseudo-agglutinations that are a source of errors in particular during test gel practices of the prior art.

According to another embodiment of the invention that is particularly suitable for phenotyping ABO, rhesus and RAI groups, the membrane 3 is impregnated by antiglobulin reagents that make possible the immobilization of all of the plasmatic antibodies of the individual.

The whole blood is deposited on a reactive zone 4 that is equipped with a filter 5 that is impregnated by agglutination reagents. The erythrocytes clump at this filter, and only the plasma reaches the porous membrane 3.

The membrane 3 then acts as a trap for the circulating plasmatic antibodies that are linked to the previously fixed antiglobulin reagents.

Test erythrocytes of antigenecity are then deposited on the membrane 3; they are allowed to act for at least 30 seconds, and a washing solution is applied so as to elute the elements that are not linked to the porous membrane 3.

When the plasmatic antibodies of the blood sample that are linked to the membrane 3 by fixing to antiglobulins recognize the corresponding test-erythrocytes, the latter are fixed and immobilized at the porous membrane 3. The result is visually reflected by a coloring that is linked to the immobilization of the applied test-erythrocytes.

When the plasmatic antibodies that are immobilized on the substrate do not recognize the test-erythrocytes, the latter are eliminated by the washing solution toward the buffer membrane.

Preferably, so as to increase the sensitivity of the test, the erythrocyte solutions can be reconcentrated.

Advantageously, the device and the process according to the invention are reliable, easy to use, and make possible a blood group phenotyping directly from a whole blood sample with previous preparation. The device is easily transportable, and the user can implement the process anywhere, without measuring equipment or centrifuging equipment. The following examples show a possible embodiment of the device according to the invention as well as its use for two complementary tests for determination of the blood group: a blood test and a serum test.

EXAMPLE 1

Embodiment of a Device According to the Invention
Porous Membrane

The porous membrane 3 is a high-density polyethylene membrane that has a pore volume of 40 to 45%, a mean pore diameter of 7 μm, and a porosity that is distributed between 1 and 14 μm.

It is delimited in the form of disks with a diameter of 6 mm and a thickness of 1 mm.

The disks are washed with pure ethanol so as to remove all of the impurities of low molecular weight and are allowed to dry in an oven at 60° C.
Filter The membrane filter 5 consists in particular of glass fibers with a diameter of 1 to 7 μm.

It is delimited in the form of disks that are 6 mm in diameter.

Absorbent Membrane

The absorbent membranes 2 are membranes that are obtained from Whatman with an absorption capacity of 198 mg/cm2.

It is delimited in the form of disks that have a diameter of 6 mm and an absorption volume that is equivalent to 50 μl of whole blood.
Solid Substrate The solid substrate 1 that makes it possible to collect the different membranes is a plastic substrate that is 12 cm in length and 8 cm in width.

It is designed to contain 72 reactive zones that are arranged in 8 columns, with each zone comprising a filter 5, a membrane 3, and a membrane 2. The columns are designed for the identification and the determination of:

Antigens A1 for column 1,
Antigens B for column 2,
Antigens AB for column 3,
Antigens D for column 5,
Anti-A plasmatic antibodies for column 6,
Anti-B plasmatic antibodies for column 7.
Columns 4 and 8 are positive controls.
Antibody Reagents The anti-A1, anti-B, anti-AB and anti-D antibody reagents are purified monoclonal antibody reagents.

They are contained in a PBS buffer solution.

They are then deposited on the membrane disks 3 that are designed to be arranged at column 1 for anti-A1, column 2 for anti-B, column 3 for anti-AB, and column 5 for anti-D, and then are put out to dry.

A washing solution that contains PBS Tween is applied on each reactive zone so as to eliminate the antibodies that are not to be linked to the membrane 3.
Antiglobulin Reagents The antiglobulin reagents are purified anti-fc antibody reagents.

The antiglobulin reagents are then deposited on the membrane disks 3 that are designed to be arranged at column 6 and column 7, and then are put out to dry.

A washing solution that contains PBS Tween is applied to each reactive zone so as to eliminate the antiglobulins that are not linked specifically to the membrane 3.
Reagents that Clump the Red Blood Cells Soybean agglutinins are prepared at a rate of 90 mg/L in the TRIS buffer at pH 7.

They are then deposited and impregnated on the filter 5 only at the column 6 and the column 7, and then are put out to dry.

EXAMPLE 2

Implementation of the Process for the Columns 1 to 5

A drop of whole blood is deposited on each reactive zone.

There is a wait of between 30 seconds and one minute, and then a washing solution is applied to elute the blood elements that are not linked specifically.

When the sample is deposited on the reactive zones of the columns 1 to 5, all of the blood elements pass through the filter 5 to reach the porous membrane 3 because the membrane 5 is lacking in reagents for clumping red blood cells. At the porous membrane 3, if the red blood cells of the blood sample bear the antigen corresponding to the antibody that is present in the reactive zone, there is a reaction for picking up and immobilizing red blood cells that is reflected by a red coloring of the reactive zone. When the red blood cells are not recognized, they are eluted toward the buffer membrane 2, which is visually reflected by an absence of coloring of the reactive zone.

EXAMPLE 3

Implementation of the Process for Columns 6 to 8

A whole blood drop is deposited on each reactive zone of the columns 6 to 8.

The red blood cells are clumped at the filter 5, and a certain amount of plasma passes through the filter and arrives at the porous membrane 3 that is impregnated with antiglobulins.

Known test erythrocytes of antigenicity are then deposited on each reactive zone.

There is a wait of between 30 seconds and one minute, and then a washing solution is applied to elute the elements of the blood that are not linked specifically.

When the plasmatic antibodies of the blood sample recognize the corresponding erythrocyte tests, the latter are fixed at the reactive zone. The result is reflected by a coloring of the reactive zone.

When the immobilized plasmatic antibodies do not recognize the test erythrocytes, the latter are eliminated by the washing solution toward the buffer membrane 2.

According to another embodiment, the test erythrocytes are incorporated into the porous membrane 3 and are kept moist by a device for protection against dehydration. When the whole blood is applied at a reactive zone, the circulating plasmatic antibodies that pass through the filter 5 are immobilized on the corresponding membrane antigens at the membrane 3 or are eluted by the washing solution.

Advantageously, the invention makes it possible to execute a Beth Vincent Test and a Simonin test on the same device without specific equipment and without prior modification of the blood sample.

According to a last aspect, the invention also relates to a kit for the identification and the determination of erythrocyte antigens of blood groups and corresponding plasmatic antibodies.

This kit comprises at least one device as described above, antibody reagents that make possible the determination and the identification of the erythrocyte antigens of blood groups, and test erythrocytes that make possible the determination and the identification of circulating plasmatic antibodies.

The invention claimed is:

1. A device for the identification and determination of blood groups and anti-blood group plasmatic antibodies from a whole blood sample, comprising:
    a solid substrate comprising at least one reactive zone on which the blood is deposited and on which a result is read, said reactive zone comprising:
    an absorbent membrane designed to absorb excess blood from a sample that is being analyzed, and
    a porous polymer membrane positioned on a top surface of the absorbent membrane, the membrane having pores with a diameter of between 1 µm to 20 µm, designed to be impregnated with a complexing reagent, for identifying said blood groups and said anti-blood group plasmatic antibodies.

2. The device according to claim 1, wherein the porous polymer membrane is a high-density polyethylene membrane.

3. The device according to claim 1, wherein the at least one reactive zone also comprises a filter.

4. The device according to claim 3, wherein the filter comprises glass fibers having a diameter of between 1 µm to 7 µm.

5. The device according to claim 1, wherein the porous polymer membrane is impregnated with a complexing agent comprising monoclonal antibody.

6. The device according to claim 3, wherein the filter is impregnated with reagents that can clump erythrocytes.

7. The device according to claim 1, wherein the porous polymer membrane is impregnated with a complexing agent comprising antiglobulin reagents that can immobilize circulating plasmatic antibodies.

8. The device according to claim 1, further comprising a reservoir that contains a washing solution and/or a revealing solution.

9. A device for identifying blood groups and anti-blood group plasmatic antibodies from a whole blood sample, the device comprising:
    a flat planar substrate comprising at least one localized reaction zone on which the blood is deposited and on which a result is read, the reaction zone comprising:
    an absorbent membrane positioned on a top surface of the substrate, the absorbent membrane designed to absorb blood; and
    a porous polymer membrane positioned on a top surface of the absorbent membrane, the porous polymer membrane having pores with a diameter between 1 to 20 µm and impregnated with a complexing reagent,
    said complexing agent comprising at least one of an anti-blood group antibody or an antiglobulin reagent that can immobilize circulating plasmatic antibodies.

10. The device according to claim 9, wherein the porous polymer membrane is impregnated with a complexing agent comprising an anti-blood group antibody selected from the group consisting of: anti-A1, anti-A2, anti-B, anti-AB and anti-D antibody.

11. The device according to claim 9, the reaction zone further comprising a filter membrane positioned on a top surface of the porous polymer membrane.

12. The device according to claim 11, wherein the filter is impregnated with reagents that can clump erythrocytes.

13. The device according to claim 11 wherein the porous polymer membrane is impregnated with a complexing agent comprising antiglobulin reagents that can immobilize circulating plasmatic antibodies.

14. The device according to claim 11, comprising at least 6 reaction zones, each reaction zone independently comprising at least one complexing agent selected from anti-A1 antibody, anti-B antibody, anti-AB antibody, anti-D antibody, anti-A plasmatic antibody and anti-B plasmatic antibody.

* * * * *

UNITED STATES PATENT AND TRADEMARK OFFICE
CERTIFICATE OF CORRECTION

PATENT NO. : 8,546,084 B2  
APPLICATION NO. : 12/667321  
DATED : October 1, 2013  
INVENTOR(S) : Najim Chaibi It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 455 days.

Signed and Sealed this

Fifteenth Day of September, 2015

Michelle K. Lee  
*Director of the United States Patent and Trademark Office*